United States Patent
Prutchi et al.

(10) Patent No.: US 6,675,043 B1
(45) Date of Patent: *Jan. 6, 2004

(54) SENSOR-BASED REGULATION OF EXCITABLE TISSUE CONTROL OF THE HEART

(75) Inventors: David Prutchi, Lake Jackson, TX (US); Yuval Mika, Zichron Yaakoc (IL)

(73) Assignee: Impulse Dynamics N.V., Curacao (AN)

( * ) Notice: Subject to any disclaimer, the term of this patent is extended or adjusted under 35 U.S.C. 154(b) by 0 days.

This patent is subject to a terminal disclaimer.

(21) Appl. No.: 09/831,283
(22) PCT Filed: Nov. 4, 1999
(86) PCT No.: PCT/IL99/00593
§ 371 (c)(1), (2), (4) Date: Sep. 10, 2001
(87) PCT Pub. No.: WO00/27475
PCT Pub. Date: May 18, 2000

Related U.S. Application Data
(60) Provisional application No. 60/107,479, filed on Nov. 6, 1998.

(30) Foreign Application Priority Data

Jan. 5, 1999 (IL) ................................. 127925

(51) Int. Cl.[7] .............................................. A61N 1/365
(52) U.S. Cl. ........................................ 607/17; 607/19
(58) Field of Search .................................. 607/9, 17–19

(56) References Cited

U.S. PATENT DOCUMENTS

| | | | |
|---|---|---|---|
| 4,554,922 A | 11/1985 | Prystowsky et al. | 607/14 |
| 5,083,564 A | 1/1992 | Scherlag | 607/9 |
| 5,213,098 A | 5/1993 | Bennett et al. | 607/18 |
| 5,284,491 A | 2/1994 | Sutton et al. | 607/17 |
| 5,514,162 A | 5/1996 | Bornzin et al. | 607/19 |
| 5,626,622 A | 5/1997 | Cooper | 607/18 |
| 5,755,740 A | 5/1998 | Nappholz | 607/18 |
| 5,792,198 A | 8/1998 | Nappholz | 607/18 |
| 5,800,464 A | 9/1998 | Kievel | 607/9 |
| 5,807,234 A | 9/1998 | Bui et al. | 600/17 |
| 5,871,506 A | 2/1999 | Mower | 607/9 |

FOREIGN PATENT DOCUMENTS

| | | | |
|---|---|---|---|
| WO | WO 97/25098 | 7/1997 | A61N/1/00 |
| WO | WO 98/10831 | 3/1998 | A61N/1/362 |
| WO | WO 98/10832 | 3/1998 | A61N/1/362 |
| WO | WO 00/04947 | 2/2000 | A61N/1/36 |
| WO | WO 00/27472 | 5/2000 | A61N/1/18 |
| WO | WO 00/27476 | 5/2000 | A61N/1/365 |

OTHER PUBLICATIONS

H. Antoni et al., "Polarization Effects of Sinusoidal 50–Cycle Alternating Current on Membrane Potential of Mammalian Cardiac Fibres", *Pflügers Arch.* 314, pp. 274–291, 1970.

(List continued on next page.)

*Primary Examiner*—Carl Layno
(74) *Attorney, Agent, or Firm*—Reed Smith LLP; William H. Dippert

(57) ABSTRACT

A method and apparatus is provided for modifying contractility of the heart of a patient. The method includes receiving signals from a sensor coupled to the body of the patient indicative of physical exertion by the patient. The signals are analyzed to estimate a metabolic demand of the patient, and excitable tissue control (ETC) stimulation is applied so as to enhance contractility of the heart muscle responsive to the metabolic need.

14 Claims, 4 Drawing Sheets

OTHER PUBLICATIONS

A.H. Foster et al., "Acute Hemodyamic Effects of Atrio–Biventricular Pacing in Humans", 1995, *The Society of Thoracic Surgeons* vol. 59, pp. 294–299.

J.L. Fleg et al., "Impact of Age on the Cardiovascular Response to Dynamic Upright Exercise in Healthy Men and Women", *J. Appl. Physiol.*, vol. 78, 1995, p. 890.

S. Cazeau et al., "Multisite Pacing for End–Stage Heart Failure: Early Experience", *Pacing and Clinical Electrophysiology* vol. 19, Nov. 1996, Part II, pp. 1748–1757.

Yu et al., "Does Biventricular Pacing Provide Better Cardiac Function than Univentricular Pacing in Normal Dogs?", Abstract, *Heart Failure Society Abstracts–on–Disk®*, Sep. 13–16, 1998, Boca Raton, Florida, one page.

A. Auricchio et al., "Acute Pacing of the Left Ventricle is Associated with Largest Hemodynamic Improvement in PATH–CHF Heart Failure Patients", Abstract, *Heart Failure Society Abstracts–on–Disk®*, Sep. 13–16, 1998, Boca Raton, Florida, one page.

C. Leclercq et al., "Comparative Effects of Permanent Biventricular Pacing in Class III and Class IV Patients", *Pacing and Clinical Electrophysiology*, Apr. 1998, vol. 21, No. 4, Part II, p. 911.

P. F. Bakker et al., "Beneficial Effects of Biventricular Pacing of Congestive Heart Failure", *PACE*, vol. 17, Apr. 1994, Part II, one page.

P. F. Bakker et al., Biventricular Pacing Improves Functional Capacity in Patients with Eng–Stage Congestive Heart Failure, *PACE*, Apr. 1995, Part II, p. 825.

"The Latest Tetralogy of Fallot Discussion with Graphical Support Including Video of Echocardiography and Catheterization", *Pediatric ElectrophysiologypicuBOOK* ("An On–Line Resource for Pediatric Critical Care"), Jul. 1996, 4 pages. (web address: http://pedsccm.wustl.edu/all–net/english/cardpage/electric/cvsurg/dysrh–8.htm).

SENSOR-BASED REGULATION OF EXCITABLE TISSUE CONTROL OF THE HEART

CROSS-REFERENCE TO RELATED APPLICATIONS

This patent application claims the benefit of U.S. Provisional Patent Application 60/107,479, filed on Nov. 6, 1998 which is assigned to the assignee of the present patent application and is incorporated herein by reference.

FIELD OF THE INVENTION

The present invention relates generally to invasive devices and methods for treatment of the heart, and specifically to devices and methods for electrical stimulation of the heart muscle.

BACKGROUND OF THE INVENTION

Typical cardiac output for a healthy adult at rest is 5 liters per minute (LPM), with a heart rate of 70 beats per minute (bpm). The stroke volume, or cardiac output per beat, in this case is about 70 ml. During exercise, the heart rate can increase by up to a factor of three, and the stroke volume can increase by about 50%. Above a certain heart rate, however, the stroke volume begins to fall off due to insufficient filling of the ventricles and other factors. Consequently, cardiac output as a function of heart rate levels off at high heart rates and may even decrease at extremely high rates.

In heart failure patients, stroke volume is typically reduced, and the fall-off of stroke volume with increasing heart rate is generally more pronounced than in healthy individuals. Thus, less oxygenated blood is available to the body, making such high heart rates even less tolerable for heart failure patients. Furthermore, driving the heart at high rates, beyond the point at which the stroke volume has begun to fall off, reduces the amount of oxygenated blood available to perfuse the heart muscle via the coronary arteries, thus increasing the risk of myocardial ischemia.

PCT patent application PCT/IL97/00012, published as WO 97/25098, to Ben-Haim et al., whose disclosure is incorporated herein by reference, describes methods for modifying the force of contraction of at least a portion of a heart chamber by applying a non-excitatory electric field to the heart at a delay following electrical activation of the portion. The non-excitatory, field is such that it does not induce action potentials in cardiac muscle cells, but rather modifies the cells response to at least the present activation. In the context of the present patent application, the use of such a non-excitatory field is referred to as Excitable Tissue Control (ETC). By suitably modifying the contraction of the heart, ETC can increase the stroke volume and thus enhance the cardiac output of patients suffering from heart failure or cardiac insufficiency due to other causes.

PCT patent application PCT/IL97/00235, whose disclosure is also incorporated herein by reference, describes a cardiac output controller using ETC stimulation. Control circuitry receives signals from one or more sensors, indicative of the heart's activity, and responsive thereto, drives stimulation electrodes to provide the ETC stimulation to the heart. The effect of the controller on cardiac output is regulated by changing the timing of an ETC stimulation pulse relative to the heart's activity, preferably relative to the heart's electrical activity or ECG signals received by one of the sensors (which comprises a sensing electrode). Alternatively or additionally, the controller changes other pulse characteristics, such as the voltage, current, duration, polarity, waveform shape and frequency, and delay of the ETC pulse relative to a pacing pulse or to sensing of an activation potential in the heart. The sensors may also include flow rate sensors, pressure sensors, temperature sensors, oxygen sensors, and other types of sensors known in the art, so as to provide additional signals indicative of hemodynamic conditions, such as cardiac output, blood pressure or blood oxygenation.

SUMMARY OF THE INVENTION

It is an object of some aspects of the present invention to provide improved methods and apparatus for Excitable Tissue Control (ETC) of the heart so as to enhance hemodynamic performance thereof.

In preferred embodiments of the present invention, a cardiac stimulation device comprises one or more ETC electrodes, at least one sensor, and electronic control circuitry, coupled to the ETC electrodes and sensor. The ETC electrodes are placed at selected sites in the heart of a patient. The sensor is placed inside the patient's body and generates signals responsive to the patient's metabolic demand and/or physical exertion. Responsive to the signals, the circuitry drives the stimulation electrodes to provide ETC stimulation so as to enhance contractility of the heart muscle. Preferably, the stimulation is provided when the actual heart rate rises above a certain threshold, which generally indicates a metabolic requirement for increased cardiac output.

In some preferred embodiments of the present invention, the circuitry receives the signals from the sensor and analyzes the signals to determine a predicted, or normative, heart rate, corresponding generally to the expected beat rate of a healthy heart at a level of metabolic demand indicated by the sensor signals. The circuitry compares the predicted heart rate to the patient's actual heart rate, which it preferably determines by analyzing signals received from electrodes coupled to the heart, most preferably from the ETC electrodes or from dedicated sensing or pacing electrodes. The circuitry drives the stimulation electrodes to provide the ETC stimulation particularly when the actual heart rate rises substantially above the predicted rate.

In some preferred embodiments of the present invention, the sensor comprises an accelerometer, and the signals generated thereby are indicative of the intensity of the patient's physical activity or exercise. Additionally or alternatively the sensor comprises a respiration sensor, preferably a minute ventilation sensor, which indicates the patient's average respiration rate and/or respiration volume. Preferably, the sensor or sensors are contained inside a can, which also contains the control circuitry and is implanted in the patient's body. It will be understood, however, that any other suitable sensor or combination of sensors may be used, and that one or more of the sensors may be outside the can, preferably located on, in or near the patient's heart.

In some preferred embodiments of the present invention, upper and lower bounds of the heart rate are established, wherein outside these bounds, the ETC stimulation is typically not applied for reasons of patient safety, or because the stimulation is not required. Within these bounds for any given predicted heart rate, upper and lower threshold values of the actual heart rate are defined which are typically, although not necessarily, respectively greater than and less than the predicted rate by predetermined factors. When the heart rate increases above the upper threshold value (without exceeding the upper bound), the ETC stimulation is initiated. When the heart rate drops below the lower threshold value, the ETC stimulation is discontinued. Between the upper and lower threshold values, a hysteresis function is applied to prevent on/off oscillation of the stimulation.

Preferably, an intensity level of the stimulation is also adjusted responsive to the actual and/or predicted heart rate, and/or to the comparison of the actual and predicted rates. Most preferably, the stimulation intensity is adjusted by varying a duty cycle of ETC stimulation pulses relative to the heartbeat. This and other suitable methods for varying and adjusting the intensity are described in Israel Patent Application 127,092, which is assigned to the assignee of the present patent application and whose disclosure is incorporated herein by reference.

The present invention thus improves safety and long-term efficacy of the ETC stimulation, by providing enhancement of cardiac contractility, and hence of hemodynamic performance, when and as indicated by the patient's metabolic needs. Controlling the ETC stimulation by this method also reduces power consumption by the device and consequently increases battery lifetime when the device is implanted in the patient's body.

Although preferred embodiments of the present invention are described in terms of certain specific types of sensors and certain methods of applying and controlling the ETC stimulation, it will be understood that the scope of the present invention is in no way limited to these modalities. The principles of the present invention may be applied using any other suitable types of sensors, ETC modalities and methods of controlling ETC stimulation, including (but not limited to) those described in the above-mentioned PCT and Israel patent applications, as well as in the U.S. patent application Ser. Nos. 09/101,723 and 09/254,902, which correspond to the PCT applications and are likewise incorporated herein by reference. Furthermore, the principles of the present invention may be adapted for use in conjunction with pacing of the heart, as described, for example, in PCT patent application PCT/IL97/00236, in the corresponding U.S. patent application Ser. No. 09/254,900, or in Israel patent application 125,424, all of which are assigned to the assignee of the present patent application and whose disclosures are incorporated herein by reference.

There is therefore provided, in accordance with a preferred embodiment of the present invention, a method for modifying contractility of the heart of a patient, including:
receiving signals from a sensor coupled to the body of the patient indicative of physical exertion by the patient;
analyzing the signals to estimate a metabolic demand of the patient; and
applying excitable tissue control (ETC) stimulation so as to enhance contractility of the heart muscle responsive to the metabolic need.

Preferably, receiving the signals includes receiving a signal responsive to motion of the patient most preferably receiving an accelerometer signal. Alternatively or additionally, receiving the signals includes receiving a signal responsive to respiration of the patient.

Preferably, the method includes measuring the patient's actual heart rate, wherein applying the signals includes comparing the actual heart rate to the metabolic demand and applying the stimulation responsive to the comparison. Most preferably, analyzing the signals includes predicting a normative heart rate responsive to the metabolic demand, and comparing the actual heart rate to the metabolic need includes comparing the actual and normative heart rates.

In a preferred embodiment, comparing the actual and normative heart rates includes:

for a given value of the normative heart rate, specifying a trigger threshold heart rate above the normative rate, and a turnoff threshold heart rate below the normative rate, thereby defining a hysteresis band intermediate the trigger and turnoff rates,
wherein applying the stimulation includes initiating the stimulation when the actual heart rate passes above the trigger rate, and suspending the stimulation when the heart rate passes below the turnoff rate.

Preferably, applying the stimulation includes controlling an intensity of the stimulation responsive to the metabolic demand.

There is further provided, in accordance with a preferred embodiment of the present invention, a method for modifying contractility of the heart of a patient, including:
specifying a trigger threshold heart rate and a turnoff threshold heart rate, which is substantially below the trigger threshold heart rate, thereby defining a hysteresis band intermediate the trigger and turnoff rates;
monitoring the patient's heart rate;
initiating excitable tissue control (ETC) stimulation so as to enhance contractility of the heart muscle when the heart rate passes above the trigger rate; and
suspending the ETC stimulation when the heart rate passes below the turnoff rate.

Preferably, the method includes specifying an upper tracking rate above the trigger threshold rate and suspending the ETC stimulation when the heart rate passes above the upper tracking, rate.

There is also provided in accordance with a preferred embodiment of the present invention, apparatus for stimulating cardiac tissue in the body of a patient, including:
at least one sensor, coupled to the body which generates signals indicative of physical exertion by the patient;
one or more electrodes which are placed in contact with the heart, and
an electrical control unit, which receives and analyzes the signals from the at least one sensor so as to estimate a metabolic demand of the patient and which applies excitable tissue control (ETC) stimulation to the electrodes so as to enhance contractility of the heart muscle responsive to the metabolic demand.

Preferably, the sensor generates a signal responsive to motion of the patient. Most preferably, the sensor includes an accelerometer. Alternatively or additionally, the sensor includes a respiration sensor.

Preferably, the control unit monitors the patient's actual heart rate, compares the actual heart rate to the metabolic demand and applies the stimulation responsive to the comparison. Most preferably, the control unit predicts a normative heart rate responsive to the metabolic demand, and compares the actual and normative heart rates so as to control application of the stimulation.

In a preferred embodiment, for a given value of the normative heart rate, the control unit determines a trigger threshold heart rate and a turnoff threshold heart rate responsive to the normative rate, the trigger threshold heart rate being higher than the turnoff threshold heart rate thereby defining a hysteresis band intermediate the trigger and turnoff rates, and
the control unit initiates application of the ETC stimulation when the actual heart rate passes above the trigger rate, and suspends the application of the stimulation when the heart rate passes below the turnoff rate.

Preferably, the control unit controls an intensity of the stimulation responsive to the metabolic need.

There is additionally provided, in accordance with a preferred embodiment of the present invention, apparatus for modifying contractility of the heart of a patient, including:

one or more stimulation electrodes, which are placed in contact with the heart; and a control unit which monitors the patient's heart rate, and which specifies a trigger threshold heart rate and a turnoff threshold heart rate, which is substantially below the trigger threshold heart rate, thereby defining a hysteresis band intermediate the trigger and turnoff rates and which initiates application of excitable tissue control (ETC) stimulation to the electrodes, so as to enhance contractility of the heart muscle, when the heart rate passes above the trigger rate, and suspends the ETC stimulation when the heart rate passes below the turnoff rate.

Preferably, the control unit specifies an upper tracking rate above the trigger threshold rate and suspends application of the ETC stimulation when the heart rate passes above the upper tracking rate.

The present invention will be more fully understood from the following detailed description of the preferred embodiments thereof, taken together with the drawings in which:

DETAILED DESCRIPTION OF PREFERRED EMBODIMENTS

Figure 1:
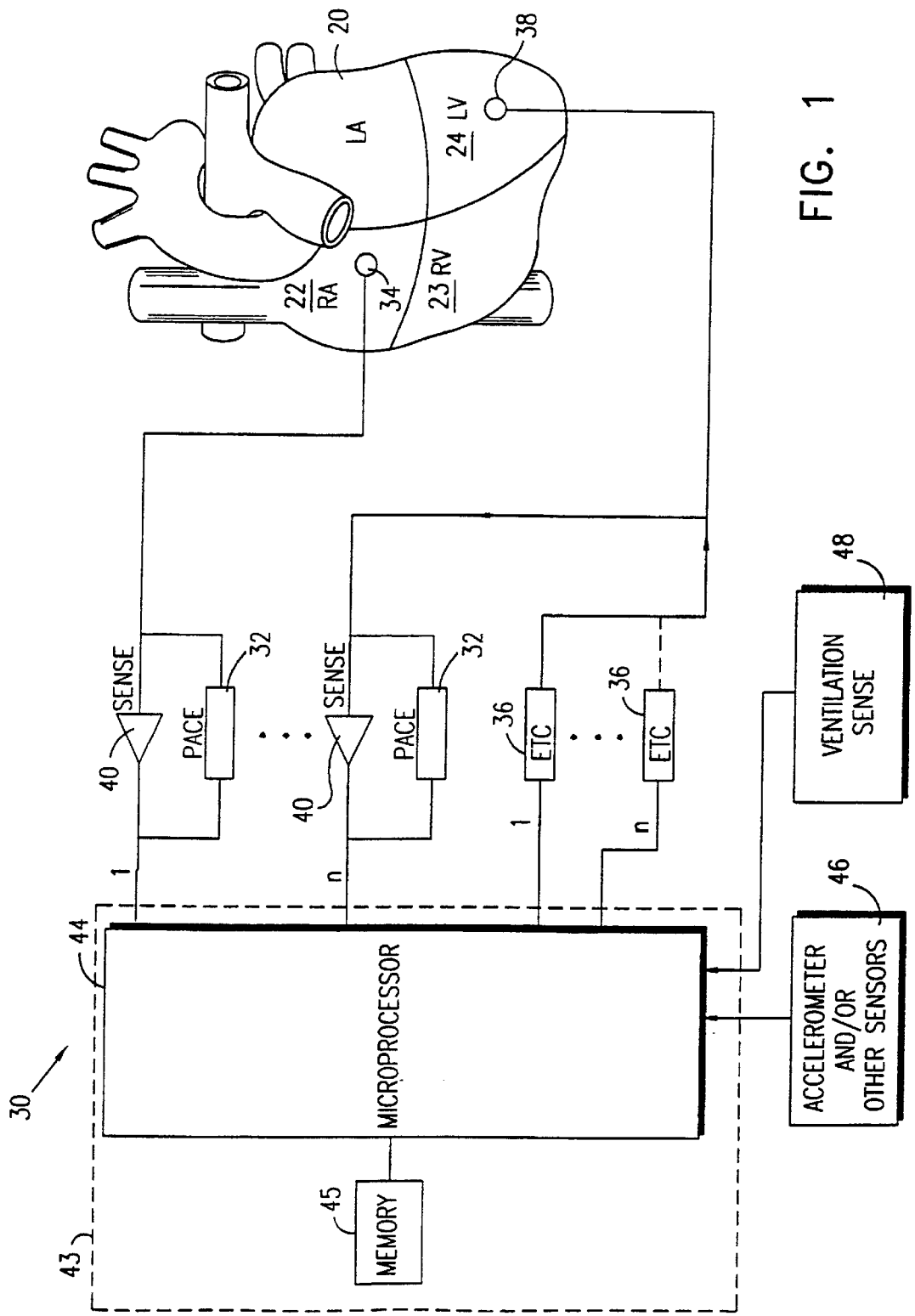
FIG. 1 is a schematic illustration of an Excitable Tissue Control (ETC) device applied to a heart, in accordance with a preferred embodiment of the present invention.

Reference is now made to FIG. 1, which is a schematic illustration showing an ETC stimulation device 30 which is applied to pace and stimulate a heart 20 of a patient, in accordance with a preferred embodiment of the present invention. Details of the design, construction and use of devices such as device 30 are provided in the above-mentioned PCT and Israel patent applications, as well as in the above-mentioned U.S. Provisional Patent Application 60/104.479.

Device 30 comprises ETC circuits 36, which are coupled to drive one or more ETC electrodes 38, preferably applied to left ventricle 24, most preferably applied epicardially or intravenously to the free wall of the left ventricle. The ETC circuits administer ETC pulses to the heart tissue so as to enhance contractility thereof. A typical ETC pulse has an amplitude of about 15 mA and a duration of about 20 ms, but it will be understood that a wide range of different waveforms may be used, as described in the above-mentioned patent applications. Optionally, the device also comprises a pacing circuit 32, coupled to one or more pacing electrodes 34, which are typically applied in right atrium 22. Greater numbers of electrodes and different electrode placements are also possible.

Sensing circuits 40 receive and process electrogram signals from heart 20, which signals are preferably provided by the pacing and/or ETC electrodes (although separate sensing electrodes can also be used for this purpose). Control circuitry 43, preferably comprising a microprocessor 44 and a memory 45, for storing programs and data, receives the signals processed by sensing circuits 40. Based on the signals, microprocessor 44 derives the heart rate and optionally, other parameters relating to cardiac function, as well. The electrogram signals also serve to indicate an activation time of the heart tissue at or near the location of ETC electrodes 38. Microprocessor 44 preferably controls ETC circuits 36 so that the ETC pulses are administered while the tissue is in a refractory state and are unlikely to have arrhythmogenic effects. Methods and circuitry for providing such control are described in a PCT patent application, filed on even date, entitled "Trigger-Based Regulation of Excitable Tissue Control in the Heart," which is assigned to the assignee of the present patent application and whose disclosure is incorporated herein by reference.

Microprocessor 44 also receives signals from other sensors coupled to the patient's body, preferably including an accelerometer sensor 46 and a minute ventilation sensor 48. These sensors provides signals to the microprocessor responsive to motion, i.e., physical activity and metabolic needs of the patient. Other sensors and corresponding measurements of any suitable type known in the art may also be used. For example, changes in blood pH and in temperature may be measured and used by microprocessor 44 in assessing physiological stress. Indications of ischemia may also be used as control inputs, primarily as danger signs to which device 30 must respond, such as a shift of the ST segment in ECG or electrogram signals or a drop in blood oxygen saturation measured in the coronary sinus. Some of these indications might also serve to change the upper tracking rate. For example, the upper tracking rate might be lowered in response to a drop in blood oxygen saturation.

Based on the sensor signals, together with patient data stored in memory 45, microprocessor 44 computes a predicted heart rate, which is a function of the patient's activity level and metabolic needs. The predicted heart rate is a normative rate at which a healthy heart would be expected to beat, given the measured activity level and metabolic need, together with personal data regarding the patient, such as age. Weight and other physiological factors. Computation of the predicted heart rate is preferably calibrated by testing the patient in the clinic to determine the appropriate proportionality of predicted heart rate to activity level and/or metabolic need, as described further hereinbelow. In patients suffering from heart disease, the actual heart rate is likely to vary substantially from the predicted rate. Responsive to the predicted heart rate, compared with the patient's actual heart rate as derived from sensing circuits 40, microprocessor 44 controls ETC stimulation to the heart, as described hereinbelow.

Figure 2:
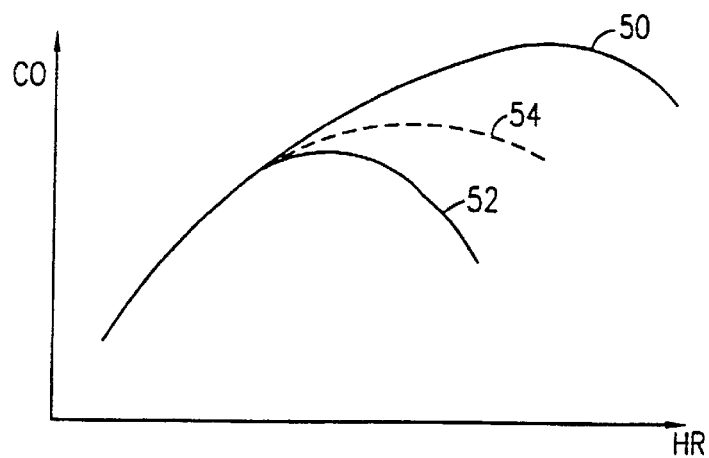
FIG. 2 is a graph that schematically shows cardiac output as a function of heart rate with and without ETC stimulation, in accordance with a preferred embodiment of the present invention.

FIG. 2 is a graph that schematically illustrates changes in cardiac output (CO) as a function of heart rate (HR) under different physiological conditions, with and without the use of device 30, in accordance with a preferred embodiment of the present invention. The scale of the graph is arbitrary. A curve 50 represents the performance of a normal, healthy heart, whereas another curve 52 represents the unassisted performance of a diseased heart, typical of heart failure patients, for example. As described hereinabove in the Background of the Invention, curve 50 shows that in the normal heart, cardiac output increases with increasing heart rate due to metabolic demand, up to a plateau as the heart rate nears its maximum. In the case of the diseased heart, however, as shown by curve 52, poor cardiac contractility causes the plateau to occur at much lower heart rate than in curve 50, and cardiac output falls off above the plateau value. In consequence, the heart failure patient is unable to exercise above a low level of exertion. Only at low heart rates does curve 52 track, more or less, the normal metabolic response reflected by curve 50.

A third curve 54 represents cardiac performance enhancement that can be achieved using device 30. At the low heart rates at which curve 52 tracks curve 50, there is no need to apply ETC stimulation to the heart, since cardiac output is adequate to meet metabolic needs without assistance. At roughly the point at which curve 52 begins to plateau and drops significantly below curve 50, the ETC stimulation is initiated, so that cardiac contractility is enhanced. As shown by curve 54, the enhancement increases the cardiac output, so that the patient is able to exercise at greater intensity, over a wider range of heart rates.

Figure 3:
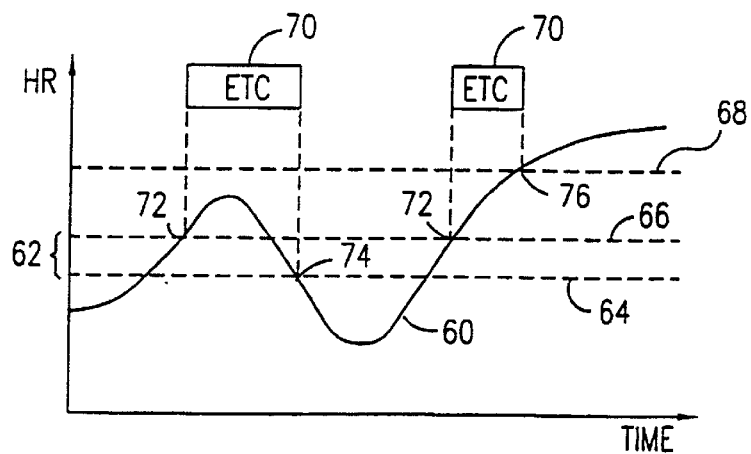
FIG. 3 is a graph that schematically illustrates application of ETC stimulation responsive to heart rate, in accordance with a preferred embodiment of the present invention.

FIG. 3 is a graph that schematically illustrates application of ETC stimulation by device 30 as a function of heart rate, in accordance with a preferred embodiment of the present invention. A curve 60 represents variations in the heart rate over time. A lower range of heart rates is defined by a hysteresis band 62, which is bounded by a trigger threshold rate 66 and a turnoff threshold rate 64. This lower range is determined such that below the range, the patient's metabolic need is generally met by the heart without ETC enhancement of contraction. When the heart rate passes above trigger threshold rate 66, at points 72 in the figure, a period of ETC stimulation, represented by a block 70, is initiated. When the heart rate drops below turnoff threshold rate 64, as shown at a point 74, the ETC stimulation is terminated. Rates 64 and 66 are preferably separated by about 5 bpm, and serve to prevent on/off oscillation of the ETC stimulation.

An upper tracking rate 68 is set as a safety measure, to prevent the application of ETC stimulation at excessively high heart rates. Such a high heart rate might occur due to a supraventricular tachycardia, rather than normal sinus rhythm. Even when the high rate is a sinus rate, application of the ETC stimulation above upper rate 68 could overwork the diseased heart and lead to myocardial ischemia. Thus, when the heart rate indicated by curve 60 passes above rate 68, the period of ETC stimulation indicated by the second block 70 is terminated.

Threshold rates 64 and 66 and upper tracking rate 68 are typically static values, which relate to the actual heart rate and do not depend on the metabolically predicted heart rate described hereinabove. Rates 64, 66 and 68 are preferably set by a physician based, inter alia, on the patient's age, sex and condition, by observing and monitoring the patient under exercise conditions in a clinical setting. Considerations of significance in regard to upper tracking rate 68 are described, for example, in an article by Fleg, et al., entitled, "Impact of Age on the Cardiovascular Response to Dynamic Upright Exercise in Healthy Men and Women," in J. Appl. Physiol. 78 (1995), p. 890, which is incorporated herein by reference. Typical values for rates 64 and 66 are in the range of 90 to 120 bpm, while rate 68 is typically in the range of 110 to 150 ppm. Alternatively, these rates may be varied dynamically in response to metabolic factors.

Figure 4:
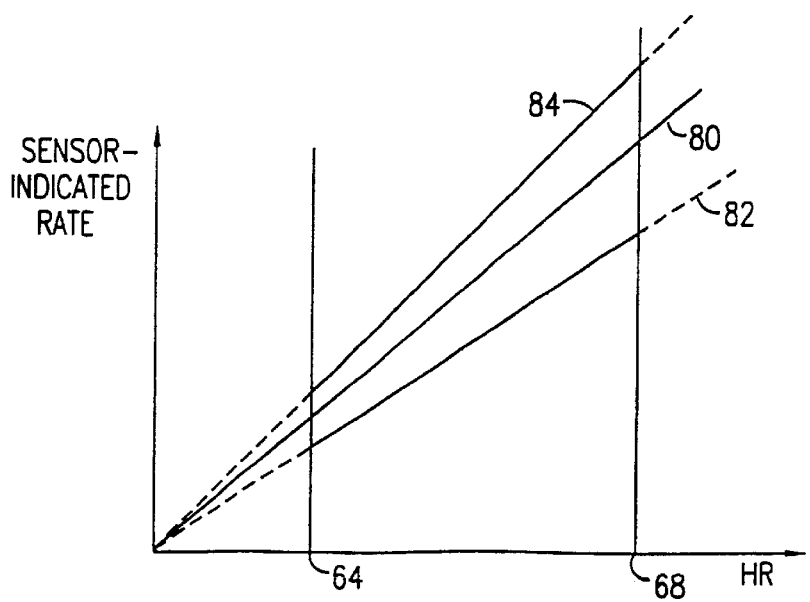
FIG. 4 is a graph that schematically illustrates a comparison between actual and sensor-indicated heart rates in accordance with a preferred embodiment of the present invention.

FIG. 4 is a graph that schematically illustrates a comparison between actual and predicted (normative, or sensor-indicated) heart rates, which is used by microprocessor 44 in controlling device 30, in accordance with a preferred embodiment of the present invention. A line 80 represents identity of the actual and predicted heart rates. Such identity reflects the ideal performance of a healthy heart and is the objective of the ETC stimulation applied by device 30 to the diseased heart. In the absence of ETC stimulation, however, the actual heart rate of the diseased heart will generally rise above the sensor-indicated rate, as the heart attempts to compensate for its inadequate contractility.

Thus, for actual heart rates in the range between turnoff threshold rate 64 and upper tracking rate 68 (wherein trigger threshold rate 66 is omitted for simplicity of illustration), microprocessor 44 activates ETC stimulation of the heart whenever the predicted, sensor-indicated rate, for a given actual heart rate, passes below a metabolic trigger threshold rate given by a lower line 82. (Equivalently, it can be said that the microprocessor activates the ETC stimulation when the actual heart rate passes above the metabolic trigger rate for a given predicted heart rate.) In this range, the actual heart rate is substantially greater than the predicted rate that is appropriate for the patient's current metabolic need. Application of the ETC stimulation will tend to increase the heart's stroke volume, so that sufficient cardiac output can be maintained at a lower actual heart rate. On the other hand, when the predicted heart rate passes above a metabolic turnoff threshold rate indicated by an upper line 84, the ETC stimulation is terminated, since in this range the stroke volume is evidently more than adequate to meet the body's needs. The range of heart rates between lines 82 and 84 acts as a hysteresis band, in a manner similar to band 62, as described hereinabove.

Figure 5A:
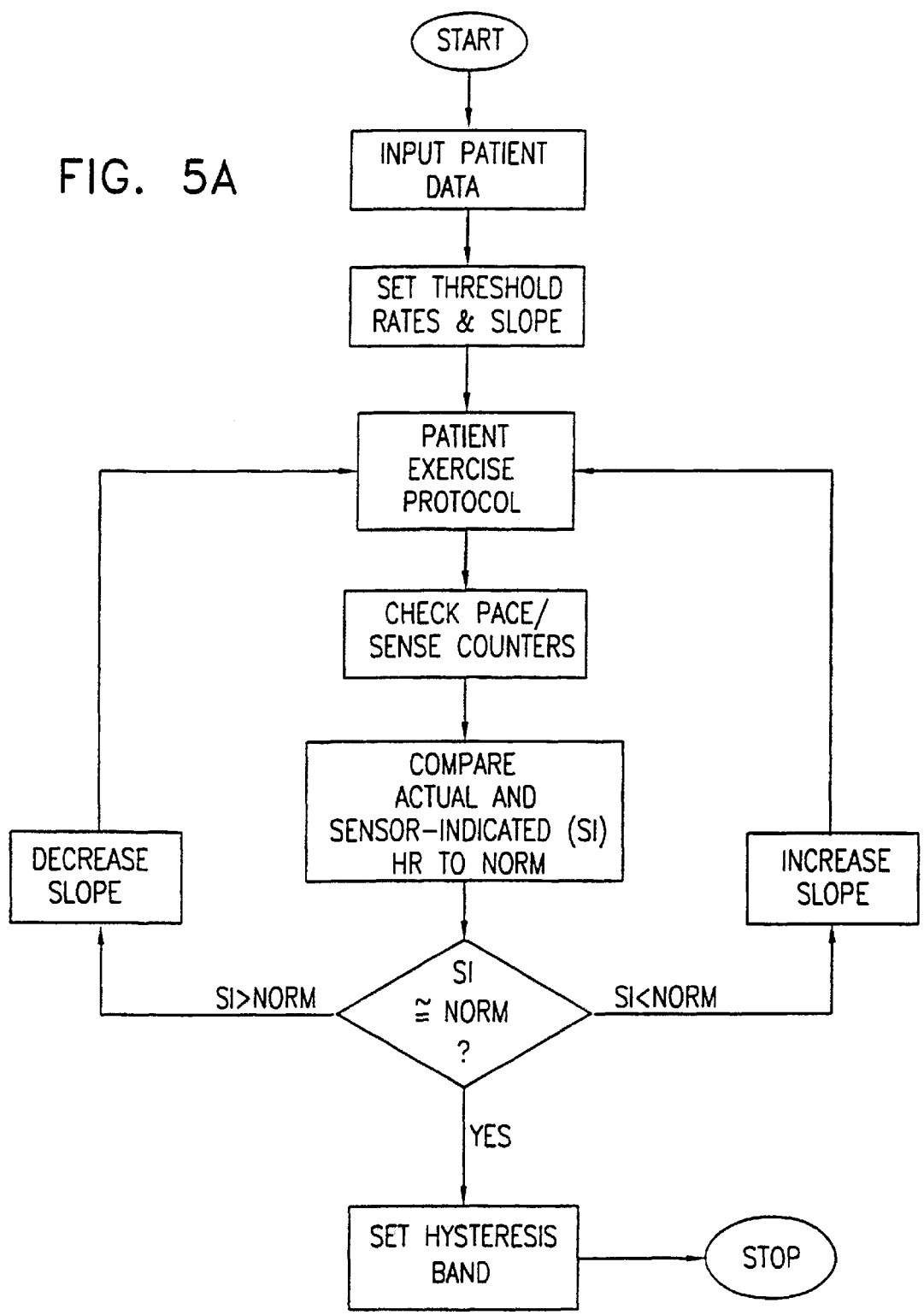
FIG. 5A is a flow chart that schematically illustrates a procedure for adjusting the device of FIG. 1, in accordance with a preferred embodiment of the present invention.

FIG. 5A is a flow chart that schematically illustrates a procedure employed by an operator, typically a cardiologist, in calibrating and adjusting device 30 after it has been implanted in the patient's body, in accordance with a preferred embodiment of the present invention. The procedure is preferably carried out using a remote programming system (not shown in the figures), as is known in the pacemaker art, to compute operating parameters and transmit them for storage in memory 45, for use thereafter by microprocessor 44 in controlling device 30. An essential purpose of the procedure is to determine an optimal functional relationship between the measured level of metabolic need and the normative, sensor-indicated heart rate that is to be used in controlling the ETC stimulation. For this purpose, the programming system preferably includes a graphic display of the actual and sensor-indicated heart rates, including recommended changes of parameter settings and their likely effects.

Figure 5B:
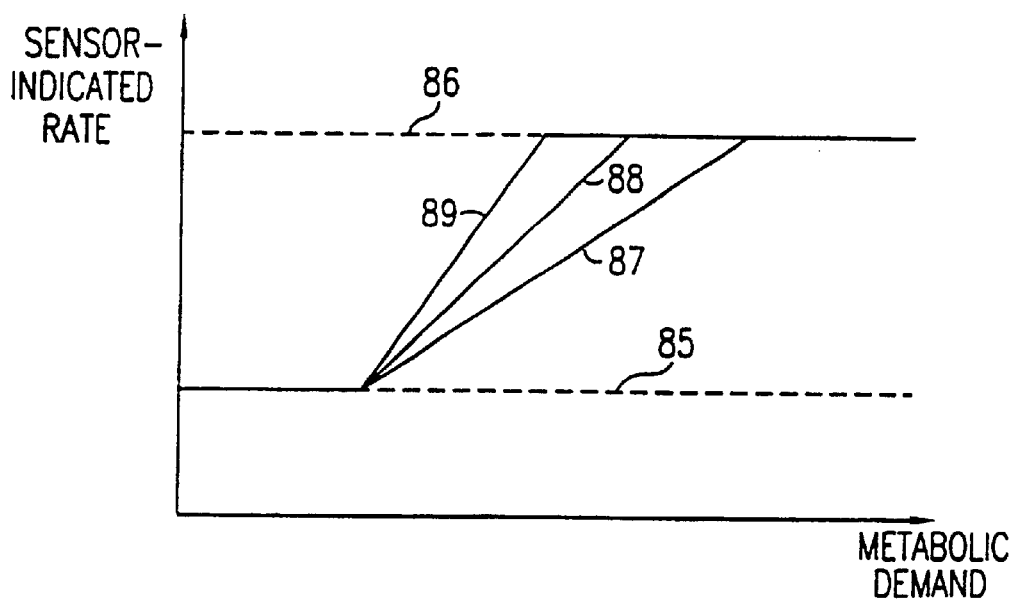
FIG. 5B is a graph that schematically illustrates functional relationships between a patient's metabolic need and sensor-indicated heart rate, in accordance with a preferred embodiment of the present invention.

FIG. 5B is a graph that schematically illustrates possible functional relationships between the metabolic need and the sensor-indicated heart rate, in accordance with a preferred embodiment of the present invention. A lower rate limit 85 and an upper rate limit 86 are defined, thus setting the minimum and maximum values of the sensor-indicated rate to be compared With the actual heart rate for controlling the ETC stimulation. Lower limit 85 preferably corresponds generally to turnoff threshold rate 64. Upper limit 86 is typically between 25% and 75% of a maximum heart rate defined for the patient's age and sex, as given, for example, in the above-mentioned article by Fleg, et al. The operator sets the upper limit dependent on the known, clinical condition of the patient's heart.

Between the lower and upper limits, the predicted, sensor-indicated heart rate is preferably linearly proportional to the level of metabolic need. The constant of proportionality, i.e., the slope of the graph, is adjusted by the operator so as to optimize the actual cardiac performance under conditions of increasing metabolic demand. By way of illustration, functional relationships with three different slopes are shown in FIG. 5B, a line 87 illustrates a low slope, line 88 a intermediate slope, and line 89 a high slope. Preferably, when a level of patient activity, as indicated, for example, by accelerometer 46, is used as the indicator of metabolic demand, there is a programmable lag in the corresponding increase of the sensor-indicated heart rate. This lag reflects the fact that in healthy individuals, the heart rate increases gradually following the beginning of physical activity, with the rate of increase dependent upon the intensity of the activity. Similarly, when activity ceases, the sensor-indicated rate should drop off gradually. More generally, it will be understood that other functional relationships between metabolic demand and sensor-indicated heart rate, not necessarily linearly proportional, may also be used.

Returning to FIG. 5A, the cardiologist begins the adjustment procedure by entering into the programming system patient data of relevance, such as the patient's age, weight, height, sex and estimated exercise capability. Based on this information, the system proposes trial values of lower limit 85, upper limit 86 and slope, for example, that of line 88, which the cardiologist may accept or modify, as appropriate. The patient then undergoes a simple exercise protocol, such as walking on a treadmill. During and/or following the protocol, the system receives and analyzes data including the patient's actual heart rate, readings of sensors 46 and 48, duty cycle (or other intensity parameters) of the applied ETC stimulation, and other telemetry data from device 30.

If device 30 is also used to pace the patient's heart, the system reads counters in the device that indicate the number of heartbeats sensed due to normal sinus rhythm compared to the number of paced beats. The procedure described herein is typically used when the number of sensed beats is much greater than the number of paced beats. The procedure must generally be modified when a substantial fraction of the beats are paced, since in such a case, the dependence of pacing rate on metabolic need may be adjusted, along with adjusting the application of ETC stimulation.

The actual and sensor-indicated heart rates at each point in the protocol are compared to a norm, indicative of the desired heart rate for the particular patient under the given exercise conditions. If on the whole, the sensor-indicated rate is lower than the norm, the typical result will be that the actual rate is above the norm. In such a case, the slope of the functional relationship between the sensor-indicated heart rate and the metabolic need is increased, for example, to that of line 89. On the other hand, if the sensor-indicated rate is above the norm, the slope should probably be decreased, to that of line 87. Following such a change in slope, the exercise protocol is preferably repeated. If the sensor-indicated rate is generally equal to the norm, and the variation of the actual heart is within desired bounds of the norm, it is assumed that the optimal slope has been found. The optimal slope may later change and be re-programmed as the patient's clinical condition changes over time. The hysteresis band defined by lines 82 and 84 (FIG. 4) is set, and the procedure is complete.

Figure 6:
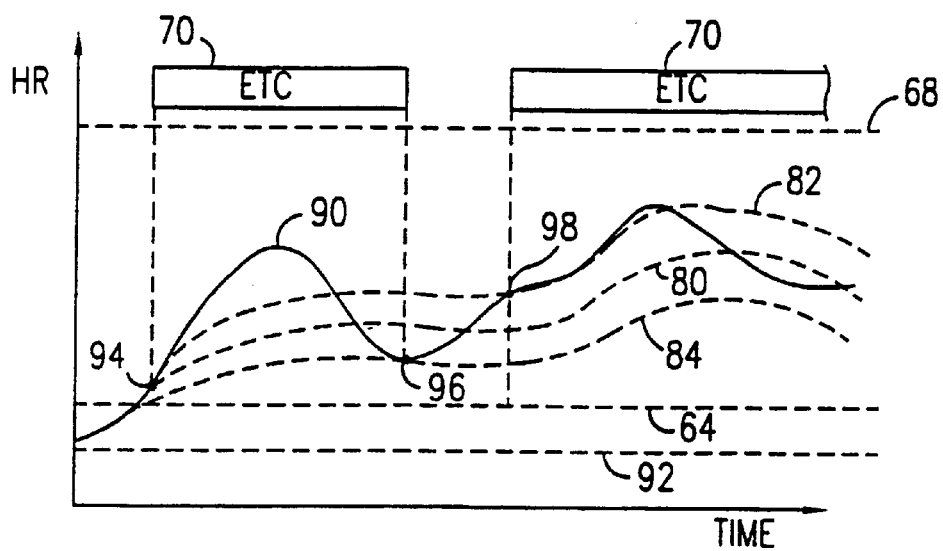
FIG. 6 is a graph that schematically illustrates application of ETC stimulation responsive to actual and sensor-indicated heart rates, in accordance with a preferred embodiment of the present invention.

FIG. 6 is a graph that schematically illustrates application of ETC by device 30 as a function of heart rate, in accordance with a preferred embodiment of the present invention corresponding to the bounds and functions shown in FIG. 4. A curve 90 represents variations in the actual heart rate over time. In addition to rates 64 and 68, a pacing threshold 92 is preferably defined, most preferably about 55 bpm, below which device 30 will also pace the heart, so as to relieve bradycardic arrhythmias. Line 80 in FIG. 4 becomes a curve 80 in FIG. 6, indicating at each point in time the predicted heart rate derived by microprocessor 44 from the readings of sensors 46 and 48. Metabolic trigger and turnoff threshold values track curve 80 in the form of curves 82 and 84, respectively.

At points 94 and 98, the actual heart rate, represented by curve 90, passes above curve 82, whereupon microprocessor 44 initiates periods of ETC stimulation indicated by blocks 70. At a point 96, curve 90 passes below curve 84, so that the ETC stimulation is discontinued. As long as the heart rate is between curves 82 and 84, the ETC stimulation is kept either on or off by hysteresis.

Preferably, the patient's metabolic need is also used as an input to increase or decrease the intensity of the ETC signals, typically by modulating the duty cycle of the signals as described hereinabove. Most preferably, the farther the actual heart rate rises above the predicted rate, the more the intensity of the ETC signals is increased. High ETC intensity is preferably also invoked when a sudden onset of physical activity is sensed, in order to prepare the heart for the impending increase in metabolic demand. Under other circumstances, to the extent possible, the ETC intensity is generally maintained at the lowest level that will bring the patient's actual heart rate within the limits of the hysteresis band around the predicted heart rate.

Although preferred embodiments of the present invention are described in terms of certain specific types of sensors and certain methods of applying and controlling the ETC stimulation, it will be understood that the scope of the present invention is in no way limited to these modalities. The principles of the present invention may be applied using any other suitable types of sensors, ETC modalities and methods of controlling ETC stimulation, including (but not limited to) those described in the above-mentioned PCT, U.S. and Israel patent applications, and may also be adapted for use in conjunction with pacing of the heart. It will thus be appreciated that the preferred embodiments described above are cited by way of example, and the fill scope of the invention is limited only by the claims.

What is claimed is:

1. A method for modifying contractility of the heart of a patient, comprising:

receiving signals from a sensor coupled to the body of the patient indicative of physical exertion by the patient;

analyzing the signals to estimate a metabolic demand of the patient;

applying excitable tissue control (ETC) stimulation so as to enhance contractility of the heart muscle responsive to the metabolic need; and measuring the patient's actual heart rate, wherein applying the signals comprises comparing the actual heart rate to the metabolic demand and applying the stimulation responsive to the comparison.

2. A method according to claim 1, wherein analyzing the signals comprises predicting a normative heart rate responsive to the metabolic demand, and wherein comparing the actual heart rate to the metabolic need comprises comparing the actual and normative heart rates.

3. A method according to claim 2, wherein comparing the actual and normative heart rates comprises:

for a given value of the normative heart rate, specifying a trigger threshold heart rate above the normative rate, and a turnoff threshold heart rate below the normative rate, thereby defining a hysteresis band intermediate the trigger and turnoff rates, and wherein applying the stimulation comprises initiating the stimulation when the actual heart rate passes above the trigger rate, and suspending the stimulation when the heart rate passes below the turnoff rate.

4. A method for modifying contractility of the heart of a patient, comprising:

specifying a trigger threshold heart rate and a turnoff threshold heart rate, which is substantially below the trigger threshold heart rate, thereby defining a hysteresis band intermediate the trigger and turnoff rates;

monitoring the patient's heart rate;

initiating excitable tissue control (ETC) stimulation so as to enhance contractility of the heart muscle when the heart rate passes above the trigger rate; and suspending the ETC stimulation when the heart rate passes below the turnoff rate.

5. A method according to claim 4, and comprising specifying an upper tracking rate above the trigger threshold rate and suspending the ETC stimulation when the heart rate passes above the upper tracking rate.

6. Apparatus for stimulating cardiac tissue in the body of a patient, comprising:

at least one sensor, coupled to the body which generates signals indicative of physical exertion by the patient;

one or more electrodes, which are placed in contact with the heart; and an electrical control unit, which receives and analyzes the signals from the at least one sensor so as to estimate a metabolic demand of the patient and which applies excitable tissue control (ETC) stimulation to the electrodes so as to enhance contractility of the heart muscle responsive to the metabolic demand, wherein the control unit monitors the patient's actual heart rate, compares the actual heart rate to the metabolic demand and applies the stimulation responsive to the comparison.

7. Apparatus according to claim 6, wherein the control unit predicts a normative heart rate responsive to the metabolic demand, and compares the actual and normative heart rates so as to control application of the stimulation.

8. Apparatus according to claim 7, wherein for a given value of the normative heart rate, the control unit determines a trigger threshold heart rate above the normative rate and a turnoff threshold heart rate below the normative rate, thereby defining a hysteresis band intermediate the trigger and turnoff rates, and wherein the control unit initiates application of the ETC stimulation when the actual heart rate passes above the trigger rate, and suspends the application of the stimulation when the heart rate passes below the turnoff rate.

9. Apparatus for modifying contractility of the heart of a patient, comprising:

one or more stimulation electrodes, which are placed in contact with the heart; and a control unit, which monitors the patient's heart rate, and which specifies a trigger threshold heart rate and a turnoff threshold heart rate, which is substantially below the trigger threshold heart rate, thereby defining a hysteresis band intermediate the trigger and turnoff rates, and which initiates application of excitable tissue control (ETC) stimulation to the electrodes, so as to enhance contractility of the heart muscle, when the heart rate passes above the trigger rate, and suspends the ETC stimulation when the heart rate passes below the turnoff rate.

10. Apparatus according to claim 9, wherein the control unit specifies an upper tracking rate above the trigger threshold rate, and suspends application of the ETC stimulation when the heart rate passes above the upper tracking rate.

11. A method for modifying contractility of the heart of a patient, comprising:

receiving signals from a sensor coupled to the body of the patient indicative of physical exertion by the patient;

analyzing the signals to estimate a metabolic demand of the patient; and applying excitable tissue control (ETC) stimulation so as to enhance contractility of the heart muscle responsive to the metabolic need, wherein receiving the signals comprises receiving a signal responsive to respiration of the patient.

12. A method for modifying contractility of the heart of a patient, comprising:

receiving signals from a sensor coupled to the body of the patient indicative of physical exertion by the patient;

analyzing the signals to estimate a metabolic demand of the patient; and applying excitable tissue control (ETC) stimulation so as to enhance contractility of the heart muscle responsive to the metabolic need, wherein applying the stimulation comprises controlling an intensity of the stimulation responsive to the metabolic demand.

13. Apparatus for stimulating cardiac tissue in the body of a patient, comprising:

at least one sensor, coupled to the body which generates signals indicative of physical exertion by the patient;

one or more electrodes, which are placed in contact with the heart; and an electrical control unit, which receives and analyzes the signals from the at least one sensor so as to estimate a metabolic demand of the patient and which applies excitable tissue control (ETC) stimulation to the electrodes so as to enhance contractility of the heart muscle responsive to the metabolic demand, wherein the sensor comprises a respiration sensor.

14. Apparatus for stimulating cardiac tissue in the body of a patient, comprising:

at least one sensor, coupled to the body which generates signals indicative of physical exertion by the patient;

one or more electrodes, which are placed in contact with the heart; and an electrical control unit, which receives and analyzes the signals from the at least one sensor so as to estimate a metabolic demand of the patient and which applies excitable tissue control (ETC) stimulation to the electrodes so as to enhance contractility of the heart muscle responsive to the metabolic demand, wherein the control unit controls an intensity of the stimulation responsive to the metabolic need.

* * * * *